US012673164B2

(12) United States Patent
Böstrom

(10) Patent No.: US 12,673,164 B2
(45) Date of Patent: Jul. 7, 2026

(54) MEDICAMENT CONTAINER SUPPORT ASSEMBLY

(71) Applicant: SHL MEDICAL AG, Zug (CH)

(72) Inventor: Anders Böstrom, Ingarö (SE)

(73) Assignee: SHL Medical AG, Zug (CH)

( * ) Notice: Subject to any disclaimer, the term of this patent is extended or adjusted under 35 U.S.C. 154(b) by 869 days.

(21) Appl. No.: 17/796,908

(22) PCT Filed: Nov. 27, 2020

(86) PCT No.: PCT/EP2020/083753
§ 371 (c)(1),
(2) Date: Aug. 2, 2022

(87) PCT Pub. No.: WO2021/164914
PCT Pub. Date: Aug. 26, 2021

(65) Prior Publication Data
US 2023/0055427 A1 Feb. 23, 2023

(30) Foreign Application Priority Data

Feb. 18, 2020 (EP) ..................................... 20157875

(51) Int. Cl.
*A61M 5/24* (2006.01)
*A61M 5/315* (2006.01)
(52) U.S. Cl.
CPC ...... *A61M 5/2425* (2013.01); *A61M 5/31511* (2013.01)
(58) Field of Classification Search
CPC ............ A61M 5/2425; A61M 5/31511; A61M 2005/2418; A61M 2005/2437; A61M 2005/2477
See application file for complete search history.

(56) References Cited

U.S. PATENT DOCUMENTS

| | | | |
|---|---|---|---|
| 8,021,335 | B2 | 9/2011 | Lesch, Jr. |
| 9,180,259 | B2 | 11/2015 | Lesch, Jr. |

(Continued)

FOREIGN PATENT DOCUMENTS

| | | |
|---|---|---|
| EP | 3381490 A1 | 10/2018 |
| WO | 2011/123024 A1 | 10/2011 |

OTHER PUBLICATIONS

International Search Report and Written Opinion for Int. App. No. PCT/EP2020/083753, mailed Feb. 4, 2021.

*Primary Examiner* — Bradley J Osinski
(74) *Attorney, Agent, or Firm* — McDonnell Boehnen Hulbert & Berghoff LLP

(57) ABSTRACT

A support assembly for a medicament container of a medicament delivery device is provided with a container support member having a proximal end and a distal end and configured to partially receive a medicament container, a deformable member arranged between a distal portion of the container support element and the proximal end of a flange of the medicament container, a rear support member arranged to be moved in contact with the distal end of the flange of the medicament container; where the deformable member is deformed by a clamping force generated by the container support member and the flange of the medicament container, such that the deformation of the deformable member is configured to compensate an engineering tolerance of the medicament delivery device.

18 Claims, 4 Drawing Sheets

(56)     References Cited

U.S. PATENT DOCUMENTS

| | | | |
|---|---|---|---|
| 2012/0143143 A1* | 6/2012 | Giambattista .......... | A61M 5/24 |
| | | | 604/192 |
| 2017/0312451 A1 | 11/2017 | Laiosa | |
| 2018/0353705 A1 | 12/2018 | Andre et al. | |
| 2021/0121634 A1* | 4/2021 | Helmer .............. | A61M 5/2033 |

\* cited by examiner

MEDICAMENT CONTAINER SUPPORT ASSEMBLY

CROSS REFERENCE TO RELATED APPLICATIONS

The present application is a U.S. National Phase Application pursuant to 35 U.S.C. § 371 of International Application No. PCT/EP2020/083753 filed Nov. 27, 2020, which claims priority to European Patent Application No. 20157875.4 filed Feb. 18, 2020. The entire disclosure contents of these applications are herewith incorporated by reference into the present application.

TECHNICAL FIELD

The present application relates to a support assembly for a medicament delivery device specifically for holding the medicament container in a steady state inside a medicament delivery device.

BACKGROUND

Regarding medicament delivery devices having a medicament container assembled therein, it is often a desire that the medicament container is supported such that it may not rattle or move inside the housing of the medicament delivery device. Due to tolerance variations of both the medicament container and the medicament delivery device as such, any support for a medicament container should preferably be flexible and possibly also resilient in order to handle forces exerted on the medicament delivery device and thus the medicament container if it e.g. is dropped onto a hard surface. Further, medicament delivery devices usually comprise a delivery member, to deliver a medicament in the medicament container to a user. The delivery member may be an integral part of the medicament container or arranged on the medicament delivery device and connected with the medicament container right before a medicament delivery operation is activated. Therefore, it is important for the distance between the front end of the medicament container to be fixed in relation to the medicament delivery device, so that the distance between the medicament delivery member and the delivery site of the user, or the distance between the medicament container and the medicament delivery member can be also fixed. A proper delivery operation or connection between the delivery member and the medicament container can be thereby provided.

The document WO 2011/123024 discloses a medicament delivery device provided with several automatic functions, which medicament delivery device has been very well received on the market. The medicament delivery device comprises a rotatable tubular operation member and a rear support member having a tubular extension part; the rotatable tubular operation member is configured to interact with the flexible tongue on the tubular extension part of the rear support member through an inner groove arranged on its inner surface; and interact with an activation member through an outer groove arranged on its outer surface for controlling the activation of the medicament delivery device. The rear support member further comprises a protrusion configured to axially hold the rotatable tubular operation member in relation to the rear support member and the medicament delivery device and a support structure in the form of arc-shaped flexible elements that are to come in contact with a distal end surface of a medicament container placed in the medicament delivery device. The support structure then exerts a force in the proximal direction of the medicament container for preventing movement of the medicament container.

This solution works very well. However, there is still room for developing more robust solutions.

SUMMARY

The aim of the present disclosure is to obtain alternative and more robust solutions.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal", "transversally" refer to a direction generally perpendicular to the longitudinal direction.

To support a medicament container in a medicament delivery device, a carrier structure is commonly used. The carrier structure is usually axially fixed to the medicament container and may be axially slidable or axially fixed to the medicament delivery device. The carrier structure is commonly designed to engage or support the medicament container at either the proximal portion, e.g. the neck portion or shoulder portion of the medicament container, or the distal portion of the medicament container, e.g. a flange portion. The medicament container is often designed to have a medicament delivery member arranged on its proximal end, and to avoid a contamination of the delivery member by the environment, there is usually a protective sheath or cap that will enclose and completely seal the medicament delivery member. Such an arrangement leads to a medicament container having a protective sheath that has a larger diameter than the barrel diameter and causes an assembly problem for the carrier structure that is arranged to support the medicament container at its proximal portion. A larger diameter of the carrier structure at its proximal portion can raise a risk that the medicament container might slip off from the carrier structure; but a smaller diameter of the carrier structure at its proximal portion might result in the protective sheath or cap of the medicament container not being able to pass through the carrier structure or damage the carrier structure when it passes. To avoid that problem, a carrier structure that supports the medicament container at its distal portion may be a straightforward solution. However, due to the engineering tolerance of manufacture, the flange of the medicament container usually has a varying thickness or different thickness in a batch of medicament containers. This tolerance issue of the thickness of the flange of the medicament container may result an inaccuracy of the distance between the medicament delivery member and a delivery site of a user.

An objective of this disclosure is to provide a simple and reliable way of axially supporting a medicament container in the medicament delivery device, compensating an engineering tolerance between the support assembly and the medicament container and keeping a more accurate distance between the medicament delivery member and the delivery site of the user.

According to an aspect of the disclosure, the objective is achieved by a robust and reliable support assembly according to claim 1.

There is hence provided a support assembly for a medicament container of a medicament delivery device, comprising: a container support member having a proximal end and a distal end and configured to partially receive a medicament container; a deformable member arranged between a distal portion of the container support member and the proximal end of a flange of the medicament container; a rear support member arranged to be moved in contact with the distal end of the flange of the medicament container; wherein the deformable member is deformed by a clamping force generated by the container support member and the flange of the medicament container, such that the deformation of the deformable member is configured to compensate an engineering tolerance of the medicament delivery device.

According to one embodiment, the container support member comprises a container support member inner structure, configured to surround the outer surface of the medicament container.

According to one embodiment, the container support member inner structure can be an enclosed structure, such as a sleeve shape or a ring shape; or a semi-enclosed structure, such as a C-shape.

According to one embodiment, the deformable member comprises a deformable member inner structure, configured to surround the outer surface of the medicament container.

According to one embodiment, the deformable member inner structure can be an enclosed structure, such as a ring shape; or a semi-enclosed structure, such as a C-shape or half circle shape.

According to one embodiment, the flange comprises a central opening, such that an inner distal edge of the central opening defined the distal inner edge of the medicament container.

According to one embodiment, the rear support member comprises a ramp surface arranged on its proximal end; wherein the ramp surface is configured to abut the distal inner edge of the medicament container.

According to one embodiment, the contact between the ramp surface and the distal inner edge of the medicament container is configured to align the rear support member with the medicament container during the medicament delivery device assembling.

According to one embodiment, the contact between the ramp surface and the distal inner edge of the medicament container is configured to prevent the medicament container from rattling in the assembled medicament delivery device.

According to one embodiment, the support assembly comprises a predetermined axial distance between the distal end of the container support member and the proximal end of the rear support member.

According to one embodiment, the support assembly is used in a medicament delivery device.

According to one embodiment, the medicament delivery device comprises a housing configured to accommodate the support assembly.

According to one embodiment, the container support member is axially and/or rotationally fixed to the housing.

According to one embodiment, the container support member is integral to the inner surface of the housing.

According to one embodiment, the rear support member comprises a distal extending tubular body; and wherein the medicament delivery device comprises a proximally biased plunger rod arranged within the tubular body.

According to one embodiment, the tubular body is arranged with a radially inward extending retaining member; wherein the biased plunger rod comprises a counter retaining member arranged on the outer surface of the biased plunger rod and configured to interact with the retaining member, such that the proximal movement of the biased plunger rod is prevented.

According to one embodiment, the radially inward extending retaining member is a ledge structure arranged on the inner surface of the tubular body.

According to one embodiment, the counter retaining member is in a recess structure.

According to one embodiment, the counter retaining member is a radial outward protrusion.

According to one embodiment, the tubular body is arranged with a proximally extending flexible arm; wherein the retaining member is arranged on the proximal end of the flexible arm.

According to one embodiment, the proximally extending flexible arm is formed on a holding element which is accommodated by the tubular body.

According to one embodiment, the proximally extending flexible arm is formed on the tubular body.

According to one embodiment, the medicament delivery device can be an injection device, an on-body device, an inhalation device, a nasal sprayer or a medical sprayer.

Other aspects, features, and advantages will be apparent from the summary above, as well as from the description that follows, including the figures and the claims.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE DRAWINGS

The specific embodiments of the disclosure will now be described, by way of example, with reference to the accompanying drawings, in which.

DETAILED DESCRIPTION

The disclosure will now be described more fully hereinafter with reference to the accompanying drawings, in which exemplifying embodiments are shown. The disclosure may, however, be embodied in many different forms and should not be construed as limited to the embodiments set forth herein; rather, these embodiments are provided by way of example so that this disclosure will be thorough and complete, and will fully convey the scope of the disclosure to those skilled in the art. Like numbers refer to like elements throughout the description.

Figure 1:
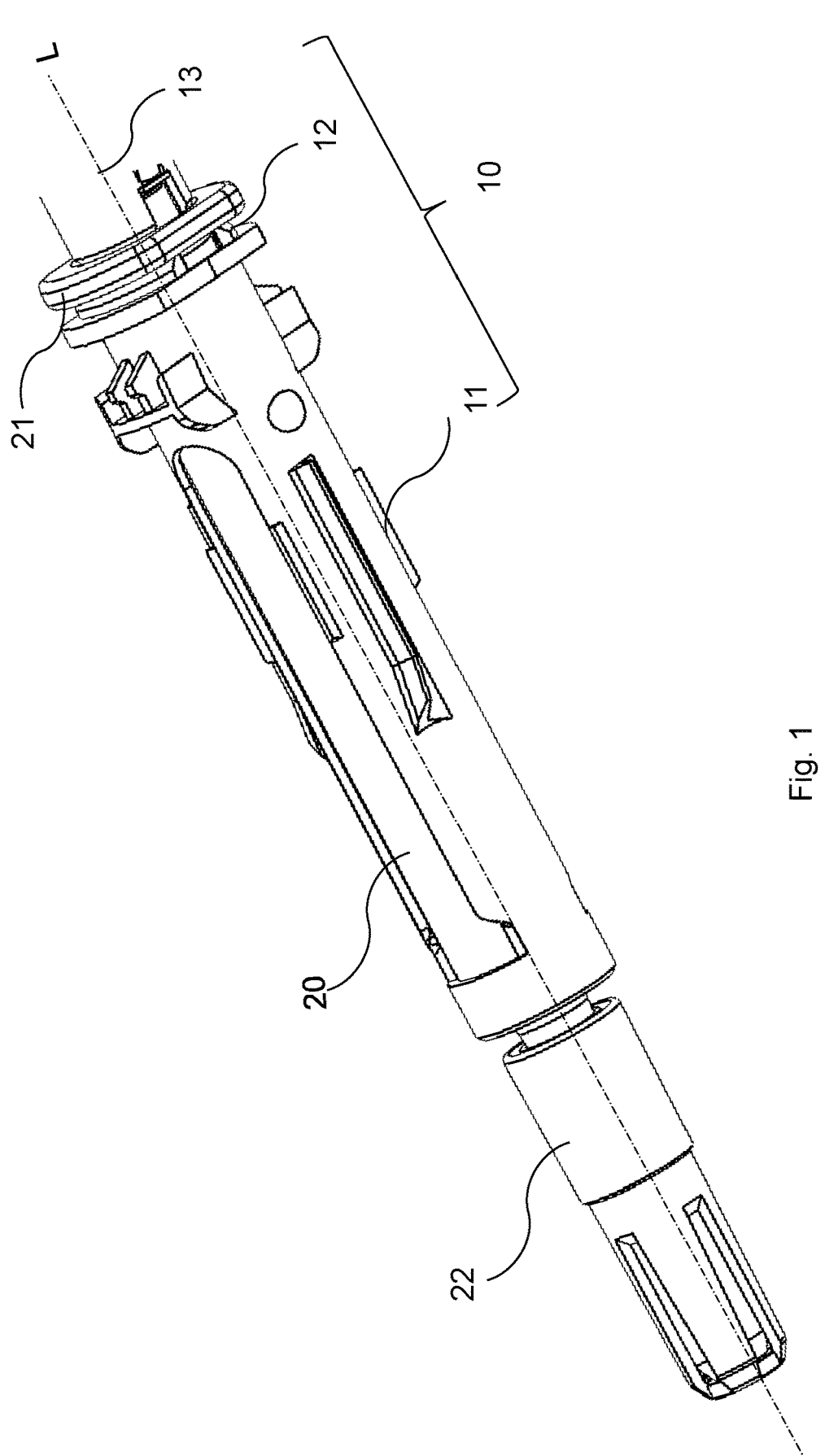
FIG. 1 displays a support assembly for a medicament container of a medicament delivery device.
Figures 3, 4:
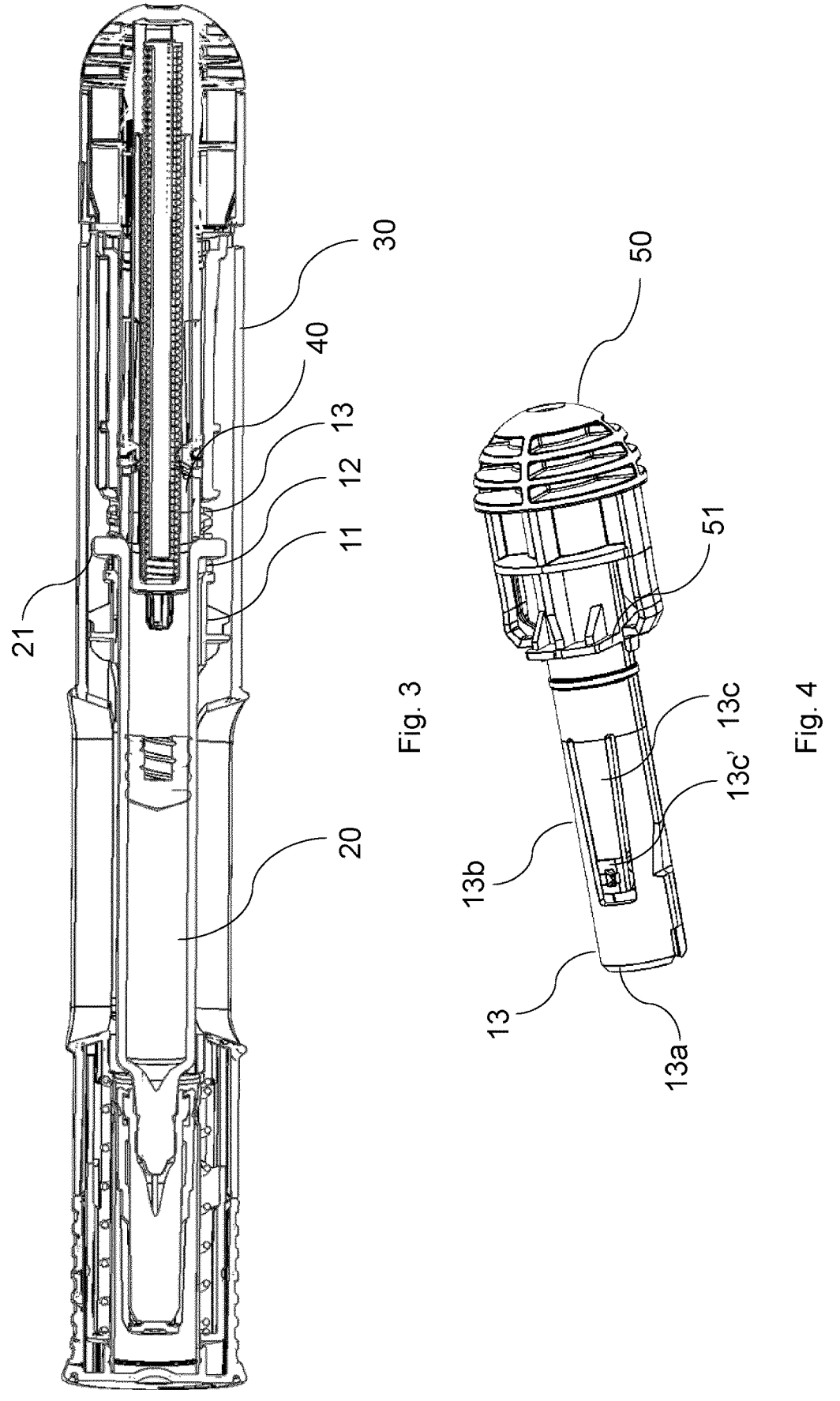
FIG. 3 displays a cross-section view of medicament delivery device with the support assembly of FIG. 1.
FIG. 4 displays a rear support member of the support assembly of FIG. 1.

FIG. 1 illustrates a support assembly 10 for a medicament container 20 of a medicament delivery device, e.g. a syringe. The medicament container 20 extends along a longitudinal axis L between a proximal end and a distal end. The medicament container 20 comprises a barrel portion configured to contain a medicament; a flange 21 with an enlarged portion arranged on the distal end of the barrel portion; a nozzle portion arranged with a medicament delivery member or to connect with a medicament delivery member, such that the contained medicament is able to be delivered through the medicament delivery member; and a seal 22 arranged to seal the nozzle portion. The support assembly 10 comprises a container support member 11, a deformable member 12, and a rear support member 13. The container support member 11 is configured to accommodate the barrel portion of the medicament container 20, and support the medicament container 20 by engaging with at least one end of the medicament container, such as the container support member 11 may support the medicament container by directly or indirectly engaging with the flange 21 of the medicament container 20. The container support member is also known as a container holder or as a container carrier. The deformable member 12 is arranged between a distal surface portion of the container support member 11 and the proximal end surface of the flange 21 of the medicament container 20. The rear support member 13 is distally arranged in relation to the medicament container 20, and is in contact with the distal end surface of the flange 21 of the medicament container 20. In a preferred embodiment, the rear support member 13 is arranged to be axially moved in contact with the distal end of the flange 21 of the medicament container 20, after the support assembly 10 and the medicament container 20 are assembled together in the medicament delivery device, as shown in FIG. 3.

The container support member 11 and the rear support member 13 are configured to exert a clamping force on the flange 21 of the medicament container 20 and the deformable member 12, such that the deformable member 12 may be deformed under the force. The deformation of the deformable member 12 is configured to compensate an engineering tolerance between the medicament container 20 and the support assembly 10.

Such as, the support assembly 10 may also be used to compensate an engineering tolerance on a medicament container due to the manufacture process of the medicament container, such that the flanges of different medicament containers may have different axial thickness or may not be even. Such engineering tolerance may also occur in a batch of medicament containers which has a generally fixed overall length, meaning the medicament containers with the length measured from the distal end of the flange to the proximal tip of the medicament delivery member is a fixed number for the whole batch of the medicament containers or only with a significantly less difference.

The support assembly 10 in this case, is arranged with a predetermined axial distance between the proximal end of the rear support member 13 and the distal end of the container support member 11. The space between the proximal end of the rear support member 13 and the distal end of the container support member 11 can be filled up by the deformable member 12 and the flange 21 of the medicament container 20. The deformable member 12 is configured to compensate the engineering tolerance of the flange 21 of the medicament container 20 by its own deformation, which is caused by the clamping force generated by the rear support member 13 and the container support member 11.

Since the distal end of the flange 21 of the medicament container 20 is in contact with the proximal end of the rear support member 13, and the overall length of every medicament containers in one batch is generally fixed, the position of the front end of the medicament container in relation to the container support member 11 can thereby be fixed, and the axial rattling of the medicament container 20 in the container support member 11 can be prevented.

The deformable member 12 may further dissipate a shock between the flange 21 and the container support member 11 generated by a sudden movement of the medicament delivery device, e.g. dropping of the medicament delivery device.

The distal surface of the deformable member 12 may be a rough surface, such that the friction between the proximal end of the flange 21 and the distal surface of the deformable member 12 can be increased, and the radial rattling of the medicament container 20 in the container support member 11 can be thereby prevented or mitigated.

Figure 2:
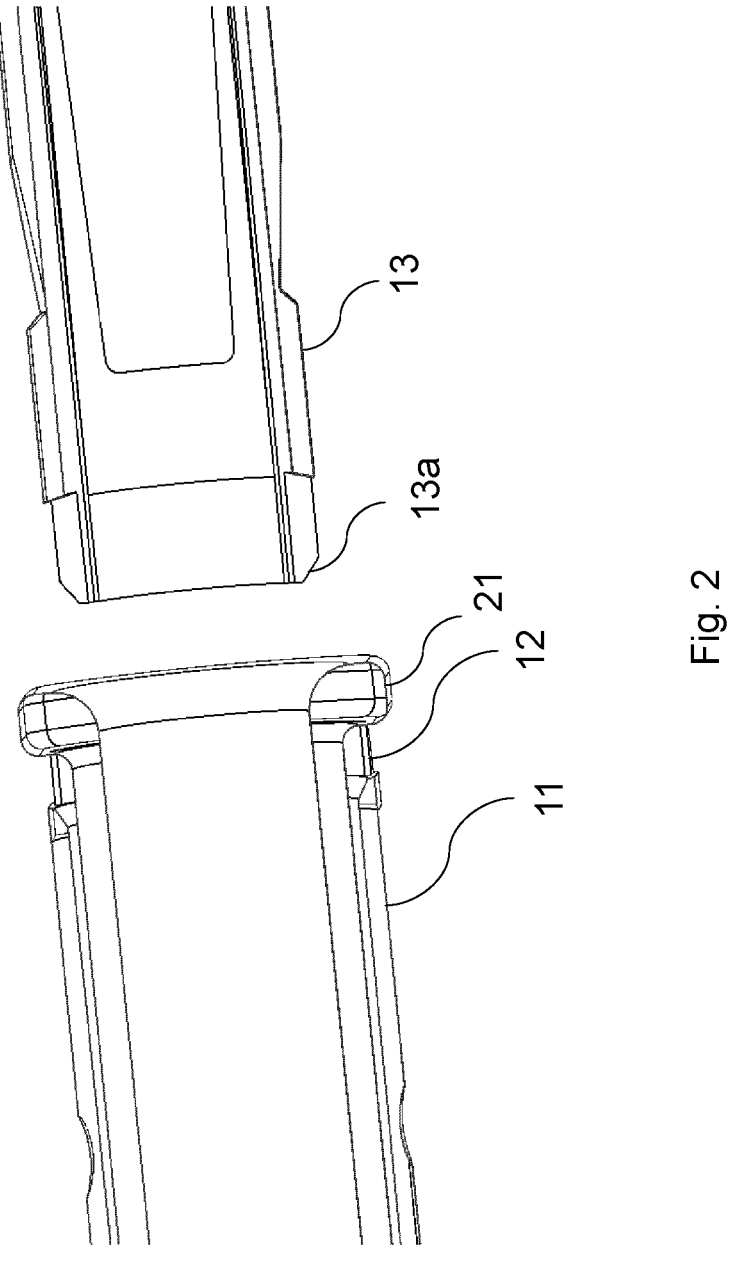
FIG. 2 displays a cross-section view of the support assembly of FIG. 1.

The rear support member 13 may further comprise a ramp surface 13a as shown in FIG. 2. The ramp surface is arranged to abut a distal inner edge of the medicament container 20 which is defined by a distal inner edge of a central opening arranged on the flange 21. The contact between the ramp surface 13a and the distal inner edge of the medicament container 20 is configured to align the rear support member 13 with the medicament container 20 during the medicament delivery device assembling and/or prevent the medicament container 20 from radially rattling in the assembled medicament delivery device.

FIG. 3 illustrates the support assembly 10 and the medicament container 20 when assembled in the medicament delivery device. The medicament delivery device may further comprise a housing 30, configured to accommodate the support assembly 10 and the medicament container 20 and a biased plunger rod 40 configured to be proximally biased to expel the medicament contained in the barrel of the medicament container 20.

The rear support member 13 may further comprise a distal extending tubular body 13b distally extending along the longitudinal axis L. A rear cap 50 may be arranged to be axially fixed or integral onto a distal portion of the tubular body 13b. The rear cap 50 comprises a ledge 51 configured to be connected to the housing 30 of the medicament delivery device.

Figure 6:
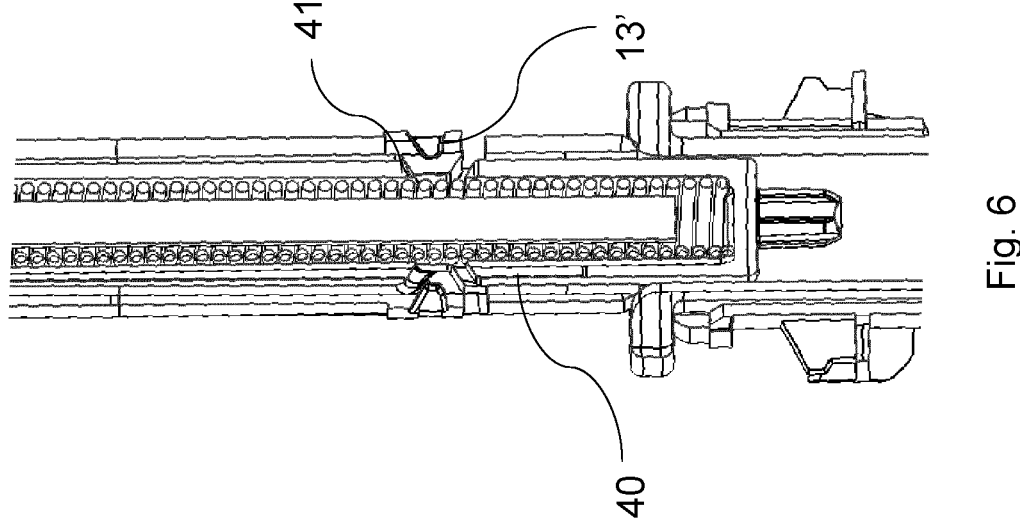
FIG. 6 displays an interaction between biased plunger rod and the rear support member.
Figure 5:
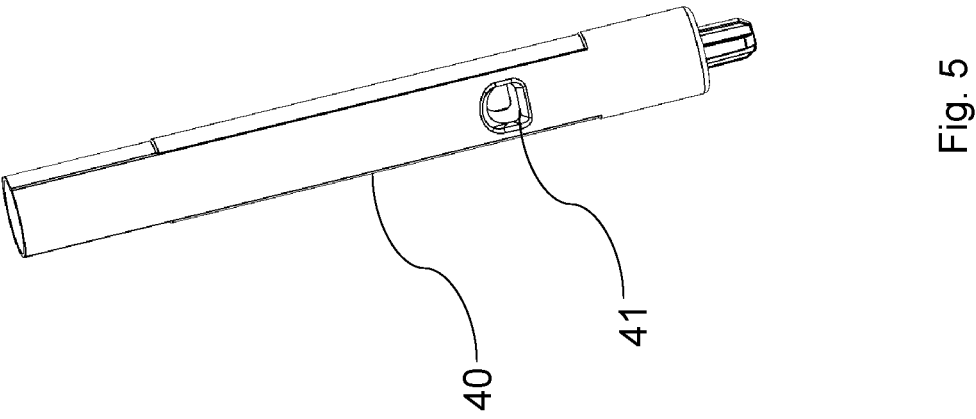
FIG. 5 displays a biased plunger rod used in the medicament delivery device.

As shown in FIG. 4, the distal extending tubular body 13b may further comprise an axially extending flexible arm 13c arranged with a fixed end which is fixed on the tubular body 13b and a free end which is radially movable in relation to the tubular body 13b. A radially inward extending retaining member 13c' is arranged on the free end of the flexible arm 13c and configured to interact with a counter retaining member 41 arranged on the outer surface of the biased plunger rod 40 which is received in the tubular body 13b as shown in FIG. 5-6. Such that, when the retaining member 13c' interacts with the counter retaining member 41, the proximal movement of the biased plunger rod 40 is prevented.

In a preferred embodiment, the extending flexible arm 13c is a proximal extending flexible arm 13c, such that free end of the flexible arm 13c is also the proximal end of the flexible arm.

The disclosure has been described above with reference to a few examples. However, as is readily appreciated by a person skilled in the art, embodiments other than the ones disclosed above are equally possible within the scope of the disclosure, as defined by the appended claims.

The invention claimed is:

1. A support assembly for a medicament container of a medicament delivery device, the support assembly comprising:
   a container support member having a proximal end and a distal end and configured to partially receive a medicament container;
   a deformable member arranged between a distal portion of the container support member and a proximal end of a flange of the medicament container; and
   a rear support member having a distal end and a proximal end, the proximal end being configured to be partially inserted into a distal end of the medicament container and arranged to be moved in contact with a distal end of the flange of the medicament container,
   wherein the deformable member is deformed by a clamping force generated by the container support member and the rear support member, such that the deformation of the deformable member is configured to compensate for an engineering tolerance of the medicament delivery device.

2. The support assembly according to claim 1, wherein the rear support member comprises a ramp surface arranged on its proximal end, and wherein the ramp surface is configured to abut a distal inner edge of the medicament container.

3. The support assembly according to claim 2, wherein the contact between the ramp surface and the distal inner edge of the medicament container is configured to align the rear support member with the medicament container during the medicament delivery device assembling.

4. The support assembly according to claim 2, wherein the contact between the ramp surface and the distal inner edge of the medicament container is configured to prevent the medicament container from rattling in the assembled medicament delivery device.

5. The support assembly according to claim 2, wherein the support assembly comprises a predetermined axial distance between the distal end of the container support member and the proximal end of the rear support member.

6. A medicament delivery device comprising a support assembly according to claim 1.

7. The medicament delivery device according to claim 6, wherein the rear support member comprises a distal extending tubular body, and wherein the medicament delivery device comprises a proximally biased plunger rod arranged within the tubular body.

8. The medicament delivery device according to claim 7, wherein the tubular body is arranged with a radially inward extending retaining member, and wherein the biased plunger rod comprises a counter retaining member arranged on an outer surface of the biased plunger rod and configured to interact with the retaining member, such that proximal movement of the biased plunger rod is prevented.

9. The medicament delivery device according to claim 8, wherein the tubular body is arranged with a proximally extending flexible arm, and wherein the retaining member is arranged on the proximal end of the flexible arm.

10. An assembly for a medicament delivery device, where the assembly comprises:
   a medicament container comprising a flange;
   a container support member partially surrounding the medicament container and having a proximal end and a distal end;
   a deformable member positioned between the distal end of the container support member and a proximal facing end of the flange; and
   a distal extending tubular body comprising a rear support member that is positioned a predetermined axial distance from the distal end of the container support member,
   wherein the rear support member comprises a distal end and a proximal end, the proximal end being arranged to be partially inserted into a distal end of the medicament container and to be moved in contact with a distal facing end of the flange of the medicament container, and
   wherein the deformable member is deformed by a clamping force generated by the container support member and the rear support member such that the predetermined axial distance is reduced when the medicament delivery device is fully assembled.

11. The assembly according to claim 10, wherein the rear support member comprises a ramp surface arranged on its proximal end.

12. The assembly according to claim 11, wherein the ramp surface abuts a distal inner edge of the medicament container.

13. An assembly for a medicament container of a medicament delivery device, the assembly comprising:
   a container support member having a proximal end and a distal end and configured to partially receive a medicament container;
   a deformable member arranged between a distal portion of the container support member and a proximal end of a flange of the medicament container; and
   a rear support member having a distal end and a proximal end, the proximal end being configured to be partially inserted into a distal end of the medicament container such as to contact a distal end of the flange of the medicament container,
   wherein the container support member and the rear support member are configured to exert a clamping force on the flange of the medicament container and the deformable member, such that the deformable member is deformed by the clamping force.

14. The assembly according to claim 13, wherein the rear support member comprises a ramp surface arranged on its proximal end, and wherein the ramp surface is configured to abut a distal inner edge of the medicament container.

15. The assembly according to claim 14, wherein the contact between the ramp surface and the distal inner edge of the medicament container is configured to align the rear support member with the medicament container during the medicament delivery device assembling.

16. The assembly according to claim 14, wherein the contact between the ramp surface and the distal inner edge of the medicament container is configured to prevent the medicament container from rattling in the assembled medicament delivery device.

17. The assembly according to claim 14, wherein the support assembly comprises a predetermined axial distance between the distal end of the container support member and the proximal end of the rear support member.

18. The assembly according to claim 13, wherein the proximal end of the rear support member contacts an interior surface of a bored portion of the distal end of the medicament container when the proximal end of the rear support member is inserted into the bored portion.

\* \* \* \* \*